United States Patent [19]

Wismann

[11] Patent Number: 4,630,666
[45] Date of Patent: Dec. 23, 1986

[54] CASTING DEVICE FOR DENTAL CASTS

[76] Inventor: Horst Wismann, Gartenstr. 22, D-8162 Schliersee, Fed. Rep. of Germany

[21] Appl. No.: 782,155

[22] Filed: Oct. 1, 1985

Related U.S. Application Data

[63] Continuation of Ser. No. 495,432, May 17, 1983, abandoned.

[30] Foreign Application Priority Data

May 19, 1982 [DE] Fed. Rep. of Germany ....... 3219008

[51] Int. Cl.[4] ...................... A61C 13/20; B22D 18/00
[52] U.S. Cl. ..................................... 164/155; 164/258; 164/335; 164/337
[58] Field of Search ............... 164/254, 256, 335, 337, 164/258, 155; 222/593, 602

[56] References Cited

U.S. PATENT DOCUMENTS

| | | | |
|---|---|---|---|
| 1,568,854 | 1/1926 | Larner | 164/256 |
| 3,081,492 | 3/1963 | Grzegorczyk | 164/254 X |
| 3,848,072 | 11/1974 | Dershem et al. | 222/593 X |
| 4,254,817 | 3/1981 | Kidowaki et al. | 164/254 X |

FOREIGN PATENT DOCUMENTS

| | | | |
|---|---|---|---|
| 535182 | 10/1931 | Fed. Rep. of Germany | 164/258 |
| 2553807 | 11/1976 | Fed. Rep. of Germany | 164/256 |
| 2635182 | 7/1977 | Fed. Rep. of Germany | . |
| 57-36060 | 2/1982 | Japan | 222/593 |

Primary Examiner—Nicholas P. Godici
Assistant Examiner—J. Reed Batten, Jr.
Attorney, Agent, or Firm—Cushman, Darby & Cushman

[57] ABSTRACT

For the preparation of dental prostheses, a casting device with a controllable casting valve on the melting crucible includes a bell, which bell can be raised and lowered and to which pressure and/or vacuum can be applied and in which several molds can be located; different operating sequences can be selected by means of an electrical control unit and, for instance independently of the casting process, pressure or vacuum can be applied to, for example, a model.

12 Claims, 8 Drawing Figures

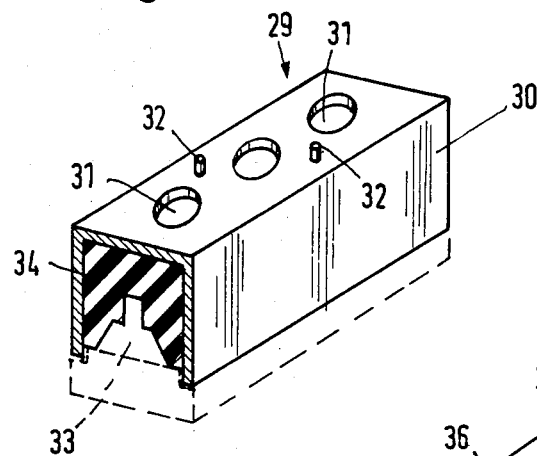
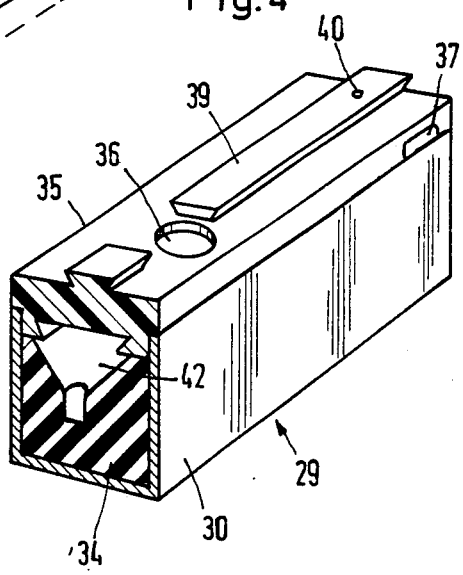
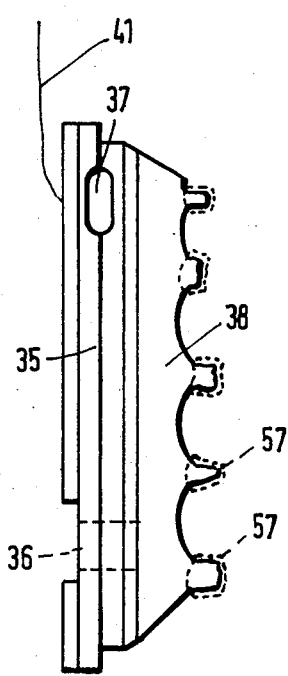

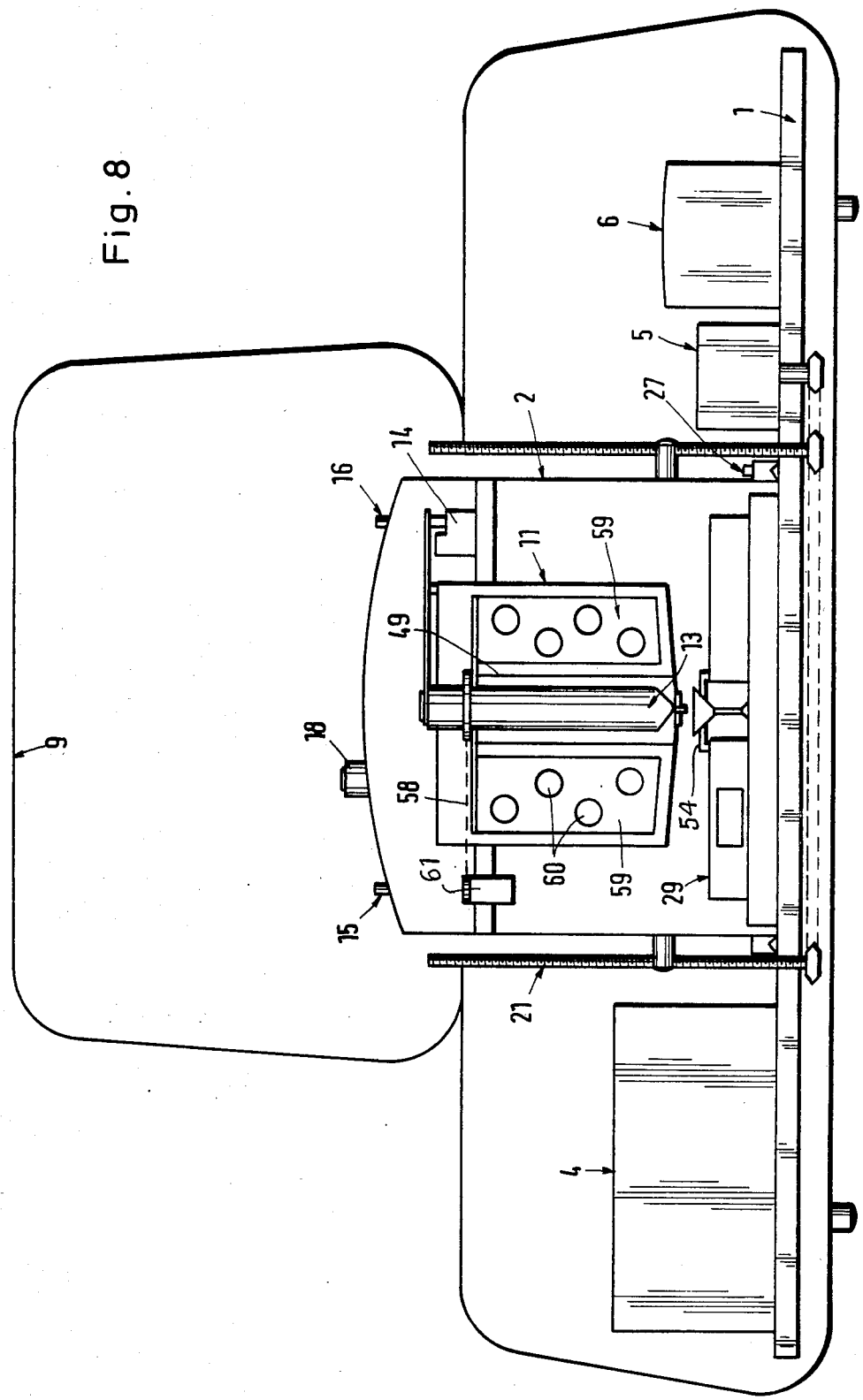

CASTING DEVICE FOR DENTAL CASTS

This is a continuation of application Ser. No. 495,432, filed May 17, 1983, which was abandoned upon the filing hereof.

The invention relates to a casting device for dental casts.

A device of this type has been disclosed by German Offenlegungsschrift No. 2,635,182, wherein the melting crucible is arranged in the casting chamber made in the form of a pot, and a casting mold can be fitted on top of this crucible, whereupon the casting mold is filled by swivelling the casting chamber through 180°. By means of an appropriate control unit, the swivelling movement can be effected automatically, and pressure or vacuum can be applied to the casting chamber. Due to the swivelling movement of the casting chamber, this known casting device is unsuitable for casting with several molds.

It is the object of the invention to design a casting device of the type set forth above, in such a way that it permits casting with several casting molds and, at the same time, can be used in a more versatile way in the preparation of a casting from a model. In particular, the device is intended to be suitable for a process in which a casting of a master model is made by means of a rubber mold from a low-melting metal, on which the desired dental prostheses are deposited in an electroplating bath. In this invention, by the provision of a casting valve, the melting crucible can be arranged in a fixed position, so that the crucible can be made larger and can be designed for filling several casting molds or one relatively large casting mold. The casting valve permits accurate metering of the casting material and hence exact control of the casting process.

The valve body arranged in the melting crucible for isolating and freeing the casting hole is advantageously provided with an electric heating device, by means of which the material used for casting can be melted in the melting crucible and can be kept molten.

To enable the casting valve to be controlled in a simple way, the valve body is actuated by a solenoid valve connected to the control unit.

The valve body, made in the shape of a rod, of the casting valve, is concentrically surrounded at a distance by a jacket which, in the closed position, rests on the bottom of the melting crucible and is provided with apertures in the lower region of the circumference. This results in more stable guiding of the valve body, when the device is switched on after a prolonged standstill.

The melting crucible can be arranged outside the casting chamber. Advantageously, the melting crucible is arranged in the casting chamber, together with the solenoid valve controlling the casting hole.

In order to enable the casting molds to be inserted and removed conveniently, the casting chamber is formed as a bell and is arranged on a plate, the bell and the plate being movable relative to one another in the axial direction. Depending on the design, the bell can be lifted off from the plate, for opening the casting chamber, or the plate below the bell can be lowered.

The relative movement between the bell and the plate is advantageously effected via at least one threaded spindle, so that reliable sealing is ensured when the casting chamber is closed and when it is subjected to pressure. The threaded spindle can here be driven by a motor which is connected to the control unit for an automatic sequence of the casting process.

To ensure reliable sealing, a tubular seal is provided between the bell and the plate, which seal can be charged with a pressurized fluid and compensates for any irregularities in the plate.

To ensure that the casting mold or casting molds will lie in the correct position underneath the casting hole of the melting crucible, recesses or projections for receiving the individual molds are provided on the plate.

For filling several casting molds, the melting crucible can be adjustable within the casting chamber, for example it can have an eccentric casting hole and be able to swivel. A simpler embodiment results from the use of a distributor which can be placed onto the casting hole of the melting crucible, so that several casting molds can be filled with a stationary arrangement of the melting crucible.

Since the casting molds have different volumes, an overflow port is provided on these molds. After a predetermined casting period, after the expiry of which even the largest casting mold has been filled, the casting process can be switched off by the control unit. It is also possible to provide a monitoring device on the overflow, which monitoring device isolates the casting valve when melt emerges.

For the preparation of a casting of low-melting metal from an original master model, the casting mold is provided with a cover which, on the underside, has an undercut recess for receiving the casting, so that the casting, after it has solidified, can be handled together with the cover.

At this stage, it is advantageous to make this cover of an electrically non-conductive material and to provide it with an electric lead which is connected to the casting. To insert the cover together with the casting fixed thereto into an electroplating bath, the cover is advantageously provided with a guide part on the outside.

Further features of the invention are indicated in the description below of an illustrative embodiment.

An embodiment of the device according to the invention is explained in more detail below, as an example, by reference to the drawing in which:

FIG. 3 shows a perspective view of a casting mold, partially in section,

FIG. 4 shows a perspective representation of the casting mold with a cover,

FIG. 5 shows a side view of the cover with a casting cast thereon,

FIG. 8 shows a cross-section, corresponding to FIG. 1, of a modified embodiment of the device.

Figure 1:
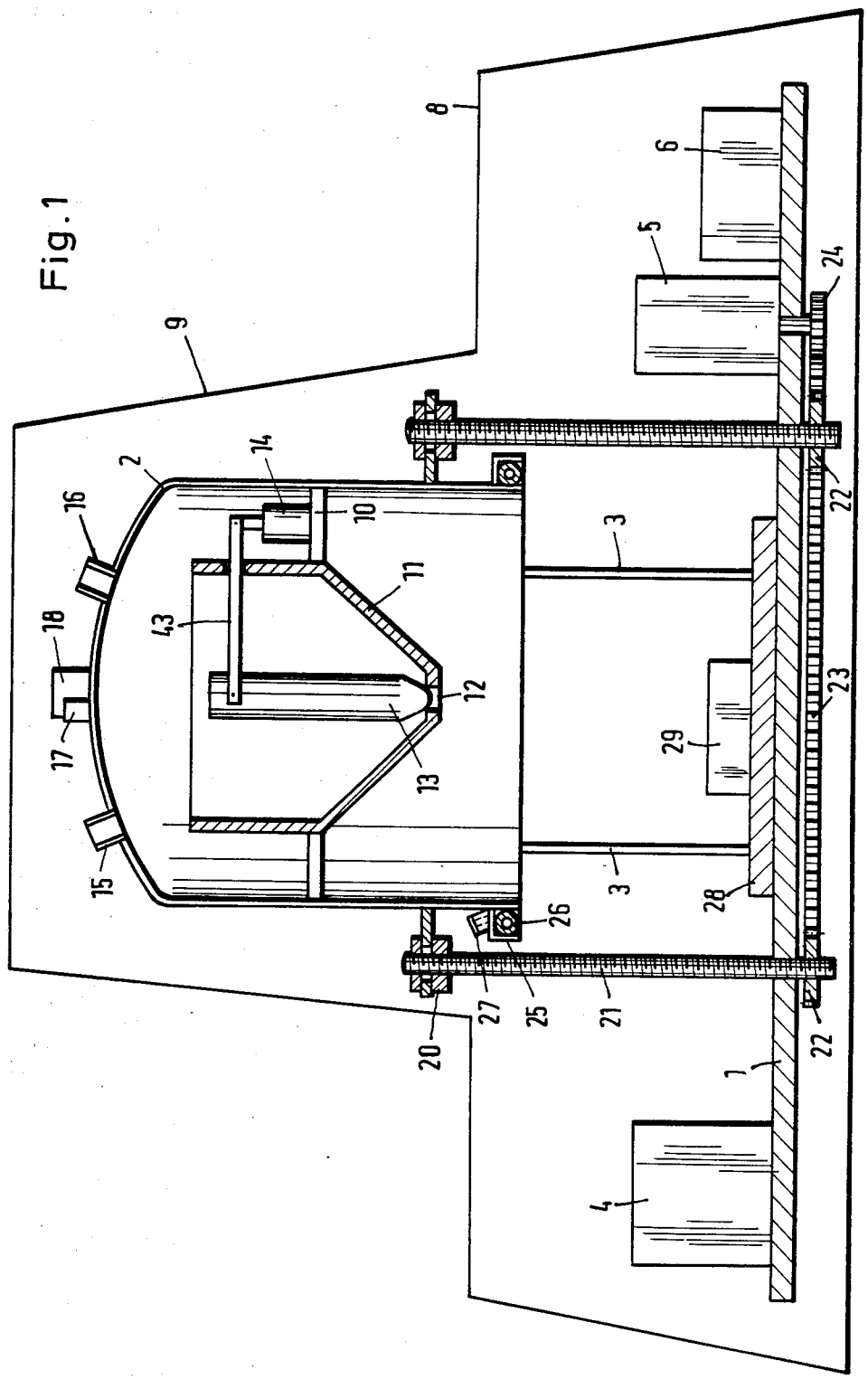
FIG. 1 shows a diagrammatic cross-section of the device.

In FIG. 1, 1 is a base plate, approximately in the middle of which a bell 2 is arranged to be displaceable in the vertical direction along guide rods 3 which are fixed to the base plate 1. An electric control unit 4, an electric motor 5, a vacuum pump 6 and a pneumatic control unit 7 are also arranged on the base plate 1. This assembly is surrounded by a housing 8 which, in the middle, has a dome 9 for receiving the upward displaced bell 2.

A melting crucible 11, in the underside of which a casting hole 12 is formed, is fixed in the bell 2 by means of radial struts 10. Above the casting hole 12, a rod-shaped valve body 13 is arranged which, by means of a lever 43 guided through the wall of the melting crucible, can be raised and lowered by a solenoid valve 14 which is located on one of the radial struts 10.

Figure 6:
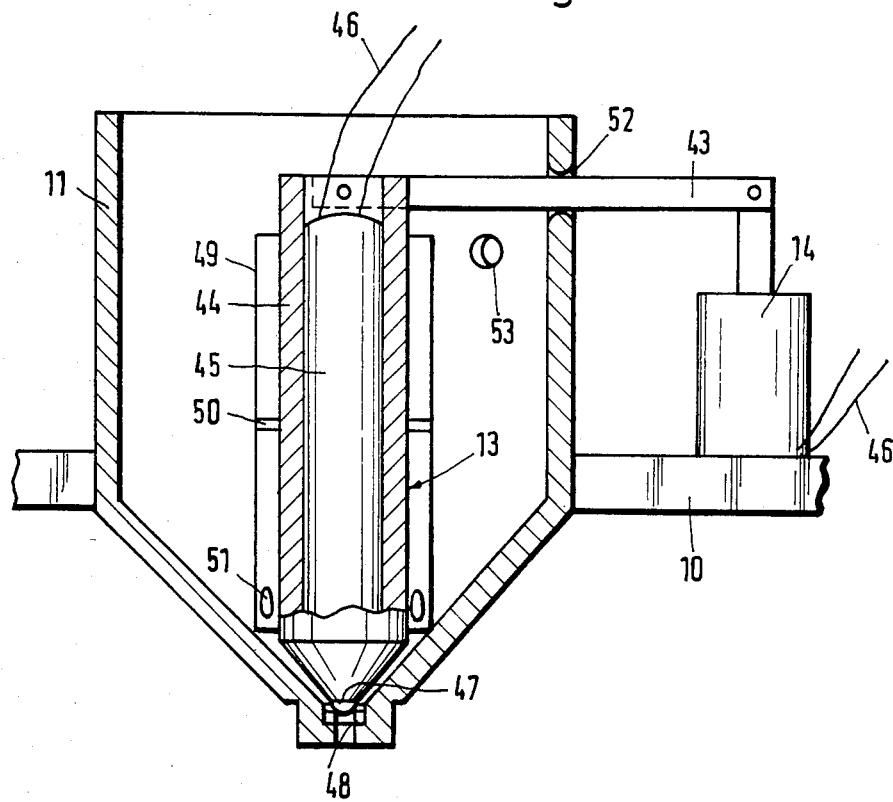
FIG. 6 shows an embodiment of the melting crucible with a casting valve.

As shown in FIG. 6, the rod-shaped valve body 13 consists of a conically tapering hollow body 44 which is closed at the bottom and can, for example, consist of brass. In the hollow body 44, an electric heating rod 45 is inserted, the connecting leads 46 of which, like those of the solenoid valve, are connected via electric contacts (not shown) to the outside of the bell 2 and to the control unit 4. A rounded tip 47 of the hollow body 44 rests on a ring 48 forming the valve seat, the conical lower part of the hollow body 44 being, in the closed position shown, at a small distance from the surrounding bottom of the melting crucible, formed in the shape of a funnel, and resting in substantially linear contact on the ring. Due to the heater built into the hollow body 44, the material in the region of the valve seat 47, 48 is always kept molten, so that the melting crucible can be reliably closed by the valve body 13.

The valve body 13 or the hollow body 44 is concentrically surrounded by a jacket 49 which is held at a distance from the hollow body 44 by radial projections 50. In the lower region, this jacket 49 is provided with apertures 51 on the circumference. In the closed position of the valve, as reproduced in FIG. 6, the jacket 49 rests on the bottom of the melting crucible 11. If the device is put into operation again after a prolonged standstill, the material in the melting crucible 11 having solidified, initially the material present between the jacket 49 and the valve body 13 is melted, and the material present outside the jacket 49 is only melted subsequently. The result of this is that, when the solidified material in the melting crucible is melted, the valve body 13 remains stable in its closed position, whilst, in the case of non-uniform melting of the material in the melting crucible, there is a risk, in particular in the lower region of the valve body 13, of the valve body 13, which substantially is only suspended in the melting crucible 11 and is not guided, being forced away to the side, whereby the casting hole is freed. The levels of the melt on the inside and outside of the jacket can be balanced through the apertures 51 in the jacket 49.

In place of the actuation of the valve body 13 via a lever 43 supported in an aperture 52 in the wall of the melting crucible, as shown, a solenoid valve can be provided which is arranged above the valve body 13 and is directly connected thereto and which at the same time serves as a guide for the valve body 13. Additionally, the valve body 13 can be stressed in the closing direction by a spring which is not shown. According to another embodiment, the valve body 13 can be provided on the top with a guide which engages in a corresponding guide part fixed to the bell 2.

Because of the lever 43 articulated to the valve body 13, in the illustrative embodiment shown, an overflow port 53 is provided below the lever in the wall of the melting crucible. On the outside, the melting crucible can additionally be provided with a heating device, for example a heating coil, which can be switched on when the device is put into operation after a prolonged standstill. By means of a temperature-monitoring instrument, which is not shown, the electric heater can be switched on via the electrical control unit 4 when the temperature of the melt falls below a predetermined value, and can be switched off again when a predetermined higher temperature is reached.

Figure 2:
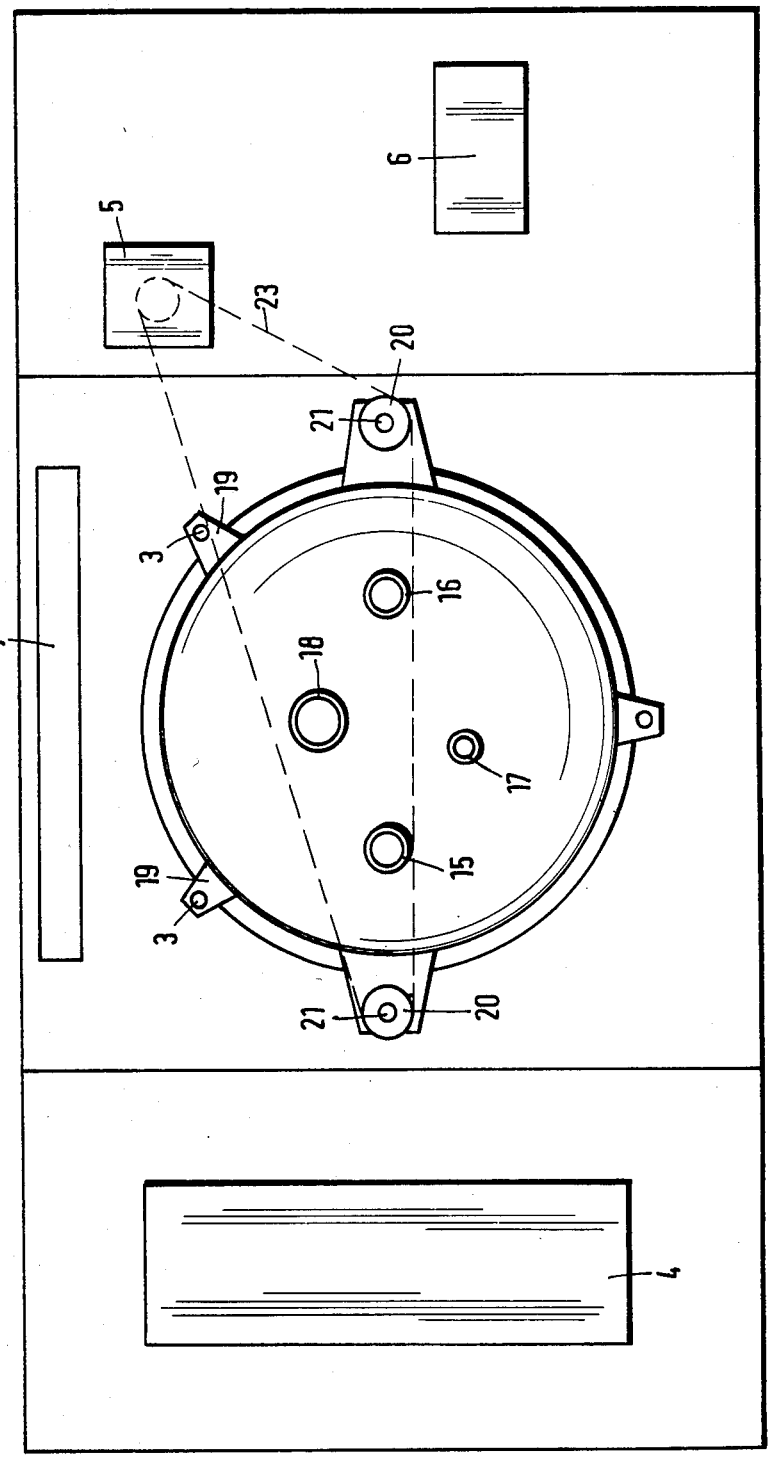
FIG. 2 shows a diagrammatic plan view of the device according to FIG. 1.

On the top of the bell, connections 15 and 16 for a pressurized gas line and a vacuum line are provided, which are not reproduced in detail. A threaded bore for a safety valve is indicated at 17, and a filling hole for the material to be melted is indicated at 18 in FIG. 2. In addition to guide lugs 19, through which the guide rods 3 are guided, nuts 20 are fixed to fork-shaped lugs on the bell 2 at diametrically opposite points, a threaded spindle 21 which is mounted in the base plate 1 to be rotatable but not displaceable in the axial direction passing through each of these nuts. On each of the ends projecting on the underside of the base plate 1, the threaded spindles 21 have a gear wheel 22 fixed, which is in engagement with a toothed belt 23 guided around a corresponding drive gear wheel 24 which can be set in rotation by the motor 5 for raising and lowering the bell 2.

On the lower rim of the bell 2, a tubular, elastic ring seal 26 which can be charged via a connection 27 with a pressurized fluid is located in an annular groove 25 of U-shaped cross-section. When the bell 2 is lowered, it is stopped, for example via a limit switch, at a small distance above the surface of the base plate 1. Subsequently, the tubular ring seal 26 is charged with pressurized fluid, so that the seal is forced against the rim of the bell 2 and against the surface of the base plate 1 and hence ensures reliable sealing. The pressure applied to the ring seal 26 is here the same as that also applied to the bell 2.

Switches for switching the device on and off, for selecting the program and the like, as well as monitoring instruments, such as a manometer, level indicator, pressure and temperature indicators and the like, are provided on the front (not shown) of the device. On the front, there is also a door through which the molds 29 can be inserted or removed, while the bell 2 is raised. On the door, a safety switch is provided which permits opening of the door only if the bell 2 is raised. For replenishing with casting material, the dome 9 can be taken off and the closure on the filling hole 18 can be undone.

FIG. 3 shows the underside of one of the casting molds 29 which can be arranged on a mold plate 28 which rests on the base plate 1 and is located within the bell 2 when the casting chamber is closed. In the illustrative embodiment shown, the casting mold 29 comprises a rectangular container 30 which is open at the top (at the bottom in FIG. 3) and on the underside of which filling holes 31 and positioning pins 32 are formed. This container 30 is first placed, in the empty state, onto a plinth which is indicated by dashed lines in FIG. 3 and which carries the master model 33 to be duplicated. Through the filling holes 31, a silicone rubber is poured in, which solidifies after a certain time and, after the master model 33 has been taken off, forms a dimensionally stable, elastic mold 34 which, in the illustration in FIG. 3, represents the negative form of the crown on a stump of a tooth. After the silicone rubber has been poured into the container 30 closed by the master model, the arrangement thus formed can be introduced into the casting chamber formed by the bell 2 and, after the bell has been lowered, subjected preferably to pressure, or alternatively to vacuum, so that bubbles contained in the liquid silicone rubber are eliminated and an exact cast obtained. After a dwell time, which can be preset by the control unit 4, the pressure or the vacuum is switched off, the bell 2 is vented and, as a result of a corresponding signal from the control unit 4, raised by the motor 5, whereupon the arrangement reproduced in FIG. 3 with the mold 34, which has solidified in the meantime, can be taken out.

Figure 7:
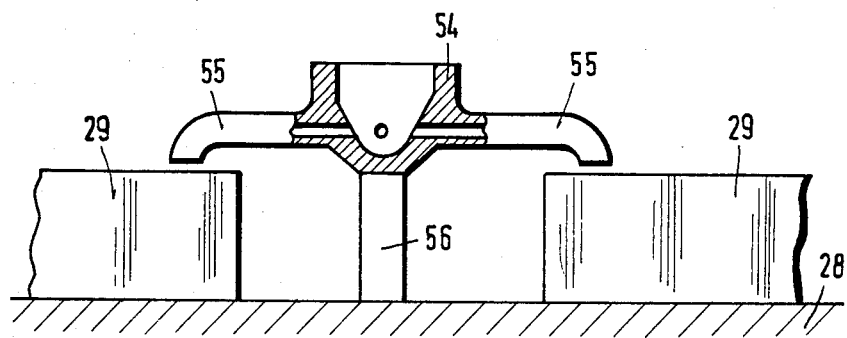
FIG. 7 shows a distributor, which can be fitted to the casting hole of the melting crucible, in the casting position.

After the container 30 with the mold 34 has been taken off the master model 33, a cover 35 (FIG. 4) is placed over the open side of the container 30, which cover consists of an electrically non-conductive, heat-resistant material, for example of polytetrafluoroethylene. This cover 35 is provided with a filling hole 36 and an overflow port 37 arranged on the side. The assembly illustrated in FIG. 4 is placed on the mold plate 28 which has bores corresponding to the positioning pins 32 so that, when an individual casting mold 29 is put in place, its filling hole 36 comes to lie underneath the casting hole 12 of the melting crucible 11. The mold plate 28 can have further bores so that, for example, four casting molds 29 arranged approximately in the form of a star on the mold plate 28 can be positioned in such a way that the filling holes 36 are each located under the outlet holes of a distributor 54 which can be attached to the casting hole 12 and is shown in FIG. 7.

The distributor 54 has an approximately funnelshaped cavity, from which distributor arms 55 lead away in radial directions. In the casting position shown, the distributor 54 rests on a stop 56 which is located on the mold plate 28 and by means of which the outlet holes on the distributor arms are positioned at a small distance above the filling holes 36 of the individual casting molds 29. Various distributors 54 having one, two, three or four distributor arms 55 can be held ready, so that one or several casting molds 29 can be filled, as desired. To fit the distributor 54 to the casting hole 12, a screw thread or a bayonet union can be provided.

After one or several of the casting molds 29 have been inserted into the assembly according to FIG. 4 on the mold plate 28, the bell 2 is lowered, after a selected program has been switched on, whereupon the ring seal 26 is charged with pressurized fluid and then a vacuum is applied initially to the bell 2 and the casting valve on the melting crucible is opened by a control pulse from the control unit 4. The melting crucible 11 contains a low-melting metal which flows into the mold 34 and, as soon as the latter is filled, emerges at the overflow port 37. A receptacle which is not shown is provided on the mold plate 28 underneath the overflow port 37. The control unit 4 can set a predetermined casting time, which ensures that each mold is filled, the material overflowing from a relatively small mold being received in the receptacle. In place of a predetermined casting time, it is also possible to provide an optical or mechanical monitoring instrument, which is not shown and which, when the melt emerges from the overflow port 37, emits a control signal to the control unit 4 for closing the casting valve.

Whilst casting takes place under vacuum, the bell 2 is subjected to pressure at the end of the casting process, so that the mold 34 is filled up exactly.

On the front (not shown) of the device, an indicator lamp is provided which lights up, via a temperature-measuring instrument, as soon as the low-melting metal in the mold 34 has solidified and is at the low temperature required for further handling. Before this, the pressure is switched off by a program preset in the control unit 4, air is admitted to the bell 2, the ring seal 26 is vented and the bell 2 is then raised by means of the motor 5.

On the underside shown in FIG. 4, the cover 35 has a recess 42 with undercut edges, so that the casting 38 (FIG. 5), formed by the solidified, low-melting metal, of the original master model 33 is firmly joined to the cover 35. As a result, the cover 35 together with the casting 38 can be taken off from the casting mold 29. In the illustrative embodiment reproduced in FIG. 5, the casting 38 comprises five individual molds of crowns on tooth stumps, which crowns are formed in an electroplating bath by the deposition of gold on the individual models. The side faces of the casting 38 and the surfaces which are located between the individual models and to which no plating is to be applied, are provided with a coating, for example a lacquer is spread on them, so that the electrodeposition takes place only in the desired zones of the model.

The cover 35 can be used for mounting the casting 38 in the electroplating bath. For this purpose, a dovetail-shaped guide 39 is formed on the top of the cover 35 (FIG. 4), by means of which guide the cover 35 together with the casting 38 can be inserted into a corresponding receiving groove of a carrier which can be immersed in the electroplating bath. Several such receiving grooves for receiving several covers 35 can be provided on such a carrier. In order to make an electrical connection to the casting 38, a bore 40 (FIG. 4) is formed in the cover 35 and, before the casting mold 29 with the cover 35 is introduced into the casting chamber, a wire 41 is inserted into this bore, which wire, during filling of the mold 34 with low-melting metal, is joined to the casting 38 thus produced. This wire 41 provided for the electrical connection in the electroplating bath can also be removed after melting-away of the casting 38 from the dental prostheses shown at 57 (in FIG. 5) by dashed lines and produced by electrodeposition, whereupon the cover 35 can be used for a further casting step.

Plastic can then be cast into the dental prostheses 57 obtained by melting the casting 38 of low-melting metal, and they can then be further processed. The casting device described can be used not only for crowns and bridges, but also for prosthesis components and the like, it also being possible to use a negative mold as the starting model instead of the positive mold of the master model, as shown.

Instead of the dovetail guide, the cover 35 can also be provided with a different push-fit connection or snap-in connection for fixing it to a carrier for the electroplating bath. Similarly, in place of the undercut recesses 42, a projection of, for example, T-shaped crosssection can be provided on the cover 35, this projection being used for joining the casting 38 to the cover 35.

Positioning pins corresponding to the positioning pins 32 can be fitted on the plinth of the master model 33, so that holding means are present on the mold plate 28 even when the assembly reproduced in FIG. 3 is inserted.

Various modifications of the type of construction described are possible. Thus, the melting crucible 11 can also be arranged outside the bell 2 and be connected to the interior thereof via a casting line. Moreover, it is possible to arrange the melting crucible 11 to be rotatable in the bell 2 and to provide it with an eccentric casting hole 12, so that several casting molds 29 can be filled one after the other by rotating the melting crucible 11.

In place of optical monitoring of the overflow 37 by means of a photoelectric barrier, it is also possible to provide a mechanical cutoff of the casting process, which cutoff interacts, for example, with the receiving container, which is not shown and is placed underneath the overflow port 37. According to another embodiment, a lever which is, for example, articulated to one of the struts 10 and is connected to a switch can be positioned on the overflow port 37. When melt emerges at the overflow 37, this lever is pivoted and, via the solenoid valve 14, switches off the casting process.

The control unit 4 can be provided with various programs for different automatic operating sequences; in this case, it is connected to the corresponding indicator devices for the filling of the melting crucible 11, the temperature, the pressure and the operating sequence. For this purpose, pressure-monitoring instruments and the like (not shown) are located on the bell 2 and/or on the mold plate 28.

Instead of a displaceably fitted bell 2, it is also possible, in a larger embodiment, to arrange the baseplate 1 in such a way that it can be lowered.

The device described can be used not only for the making of dentures, prostheses and the like, but also for other casting processes, such as, for example, the making of jewellery from a model, and the like. The device described can then be used not only for casting purposes, but also for applying pressure or vacuum, as was explained by reference to the arrangement according to FIG. 3.

For the application of pressure, an existing compressed-air source can be envisaged. It is likewise possible to use a gas for this purpose, if casting is to be carried out in an inert atmosphere or pressure is to be applied. Particular programs can be preset by means of a microprocessor arranged in the control unit 4, so that various operating sequences with application of pressure or vacuum and a casting process can proceed automatically.

The device can be designed for applying pressures of up to 18 bar. The vacuum which can be applied depends on the performance of the vacuum pump 6. In the process described, the casting material used is a metal which melts at about 95°. The heating on the melting crucible 11 can be designed in such a way that heating temperatures of up to 1,000° can be attained, so that it is not necessary to work only with low-melting material.

FIG. 8 shows an embodiment of the deivce, wherein an agitator is arranged in the melting crucible 11. On one of the struts 10, an electric motor 61 is mounted which, via a chain drive or belt drive 58, drives stirrer blades 59 which are mounted rotatably on the valve body 13. The stirrer blades 59 are provided with perforations 60.

FIG. 8 shows the bell 2 with the melting crucible 11 in the lowered state, the distributor 54 reproduced in detail in FIG. 7 being arranged between the casting molds 29.

I claim:

1. A casting device for making dental casts with low melting metals or alloys comprising a casting chamber in the form of a bell having a rim and an external surface, means for sealing the casting chamber in a pressure-tight manner including a plate, said bell being liftable and lowerable relative to said plate by lifting means and having connection means for connection to a source of pressure and to vacuum means, said means for sealing further including a fluid pressure actuated sealing member disposed on said external surface of said bell and adjacent and surrounding said rim so that said sealing member will seal against both said rim and said plate when said bell is lowered to engage said plate and said sealing member is actuated, a melting crucible mounted in said bell and being movable with said bell, said bell being provided with a filling hole for material to be melted, said crucible having a discharge opening and a casting valve means mounted in said crucible for movement toward said discharge opening to close said opening and away from said opening by means of a solenoid mounted in said bell, an agitator disposed in said crucible, driving means mounted in said bell for driving said agitator, said casting device further including means for automatically controlling the operation of said device.

2. A casting device as claimed in claim 1, wherein the valve means (13) is operably connected to said solenoid (14) connected to the controlling means (4).

3. A casting device as claimed in claim 1, wherein the valve means (13) made in the shape of a rod is concentrically surrounded at a distance by a jacket (49) which, in the closed position, rests on the bottom of the melting crucible (11) and is provided with radial apertures (51) in the lower region of the circumference.

4. A casting device as claimed in claim 1, wherein a mold plate (28) with receiving means for the insertion of a casting mold is provided.

5. A casting device as claimed in claim 1, wherein a distributor is attached to the discharge opening (12) of the melting crucible.

6. A casting device as claimed in claim 1, wherein the lifting means comprises at least one threaded spindle (21) provided between the bell (2) and the plate (1).

7. A casting device as claimed in claim 6, wherein the threaded spindle is driven by an electric motor (5).

8. A casting device as claimed in claim 1, wherein a casting mold (29) is provided, said casting mold having an overflow port (37).

9. A casting device as claimed in claim 8, wherein the casting mold (29) is provided with a cover (35) which, on the underside, has an undercut recess (42) or a projection for fixing a solidified casting (38).

10. A casting device as claimed in claim 9, wherein the cover (35) consists of an electrically non-conductive material and is provided with an electrically conductive terminal (41) which is conductively connected to the casting (38).

11. A casting device as claimed in claim 9, wherein the cover (35) is provided with a guide (39) on its top.

12. A casting device as claimed in claim 11, wherein the overflow port (37) is formed on the cover (35).

* * * * *